(12) United States Patent
Tranchina

(10) Patent No.: US 8,239,044 B1
(45) Date of Patent: Aug. 7, 2012

(54) STIMULATION LEAD FOR STEERING CURRENT FOR STIMULATION OF PATIENT TISSUE, METHOD OF STIMULATING PATIENT TISSUE, AND IMPLANTABLE MEDICAL SYSTEM

(75) Inventor: Benjamin A. Tranchina, Allen, TX (US)

(73) Assignee: Advanced Neuromodulation Systems, Inc., Plano, TX (US)

( * ) Notice: Subject to any disclaimer, the term of this patent is extended or adjusted under 35 U.S.C. 154(b) by 774 days.

(21) Appl. No.: 12/329,154

(22) Filed: Dec. 5, 2008

Related U.S. Application Data

(60) Provisional application No. 61/012,083, filed on Dec. 7, 2007.

(51) Int. Cl.
*A61N 1/18* (2006.01)

(52) U.S. Cl. ............ 607/118; 607/1; 607/2; 607/3; 607/115; 607/116; 607/66

(58) Field of Classification Search ............ 607/1–3, 607/115–116, 118
See application file for complete search history.

(56) References Cited

U.S. PATENT DOCUMENTS

| | | | |
|---|---|---|---|
| 5,417,719 A | 5/1995 | Hull et al. | |
| 6,754,539 B1 | 6/2004 | Erickson et al. | |
| 6,999,820 B2 | 2/2006 | Jordan | |
| 7,096,063 B2 * | 8/2006 | Wanasek et al. | 607/5 |
| 2006/0167525 A1 * | 7/2006 | King | 607/46 |
| 2008/0140168 A1 | 6/2008 | Walter et al. | |

\* cited by examiner

*Primary Examiner* — Carl H Layno
*Assistant Examiner* — Deborah Malamud
(74) *Attorney, Agent, or Firm* — Christopher S. L. Crawford; Craig Hoersten; Peter R. Lando

(57) ABSTRACT

In one embodiment, a method of electrically stimulating neural tissue of a patient, comprises: generating, by an implantable pulse generator, one or more electrical pulses; applying the one or more electrical pulses to neural tissue of a patient using one or more electrodes of one or more stimulation leads; concurrently with the generating, providing a voltage waveform or signal by the implantable pulse generator; and concurrently with the applying, electrically coupling one or more field effect electrodes of the one or more stimulation leads to the voltage waveform or signal to generate a localized electric field within tissue proximate to the one or more electrodes used to apply the one or more electrical pulses.

3 Claims, 6 Drawing Sheets

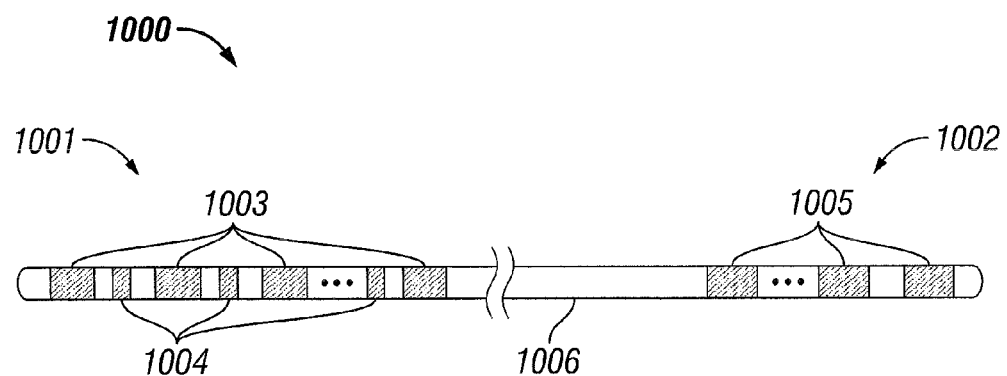
FIG. 10
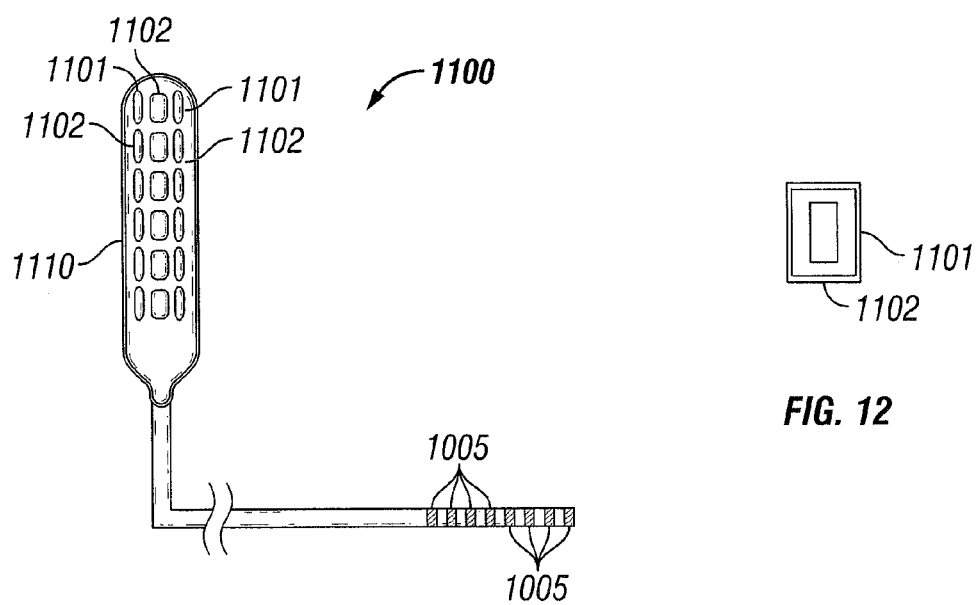
FIG. 11
FIG. 12

STIMULATION LEAD FOR STEERING CURRENT FOR STIMULATION OF PATIENT TISSUE, METHOD OF STIMULATING PATIENT TISSUE, AND IMPLANTABLE MEDICAL SYSTEM

CROSS-REFERENCE TO RELATED APPLICATIONS

This application claims the benefit of U.S. Provisional Application No. 61/012,083, filed Dec. 7, 2007, the disclosure of which is incorporated herein by reference.

BACKGROUND

Neurostimulation systems are devices that generate electrical pulses and deliver the pulses to nerve tissue to treat a variety of disorders. Spinal cord stimulation (SCS) is an example of neurostimulation in which electrical pulses are delivered to nerve tissue in the spine, typically for the purpose of treating chronic pain. While a precise understanding of the interaction between the applied electrical energy and the nervous tissue is not fully appreciated, it is known that application of an electrical field to spinal nervous tissue can effectively mask certain types of pain transmitted from regions of the body associated with the stimulated nerve tissue. Specifically, applying electrical energy to the spinal cord associated with regions of the body afflicted with chronic pain can induce "paresthesia" (a subjective sensation of numbness or tingling) in the afflicted bodily regions. Thereby, paresthesia can effectively mask the transmission of non-acute pain sensations to the brain.

Neurostimulation systems generally include a pulse generator and one or several leads. The pulse generator is typically implemented using a metallic housing that encloses circuitry for generating the electrical pulses. The pulse generator is usually implanted within a subcutaneous pocket created under the skin by a physician. The leads are used to conduct the electrical pulses from the implant site of the pulse generator to the targeted nerve tissue. The leads typically include a lead body of an insulative polymer material with embedded wire conductors extending through the lead body. Electrodes on a distal end of the lead body are coupled to the conductors to deliver the electrical pulses to the nerve tissue.

The effectiveness of a neurostimulation therapy is dependent upon recruiting the appropriate nerve fibers for stimulation while avoiding unrelated nerve fibers (e.g., the nerve fibers corresponding to areas without pain or corresponding to motor functions). Accordingly, it has been proposed to "steer" current in an attempt to localize the specific nerves that will be stimulated by the electrical pulses. As currently known in the art, there are two different methods of steering current. In one embodiment, pulse amplitude "fractionalization" or "tripolar" stimulation is applied. In such techniques, anodes of varying amplitudes are placed on either side of a cathode. The superposition of the fields created by the tripolar arrangement tend to laterally shape or steer the locus of stimulation. Another technique applies stimulation multiple pulses in a non-simultaneous manner using different electrode combinations. However, the pulses are provided within a sufficiently small amount of time that the combined effect of the multiple pulses tend to create a locus of stimulation that depends upon the relative amplitude of the pulses and the timing between the pulses.

SUMMARY

In one embodiment, a method of electrically stimulating neural tissue of a patient, comprises: generating, by an implantable pulse generator, one or more electrical pulses; applying the one or more electrical pulses to neural tissue of a patient using one or more electrodes of one or more stimulation leads; concurrently with the generating, providing a voltage waveform or signal by the implantable pulse generator; and concurrently with the applying, electrically coupling one or more field effect electrodes of the one or more stimulation leads to the voltage waveform or signal to generate a localized electric field within tissue proximate to the one or more electrodes used to apply the one or more electrical pulses, wherein the one or more field effect electrodes are adapted to prevent conduction of current through the one or more field effect electrodes. In another embodiment, a magnetic element is disposed between electrodes of a stimulation lead to steer current more deeply into neural tissue.

The foregoing has outlined rather broadly certain features and/or technical advantages in order that the detailed description that follows may be better understood. Additional features and/or advantages will be described hereinafter which form the subject of the claims. It should be appreciated by those skilled in the art that the conception and specific embodiment disclosed may be readily utilized as a basis for modifying or designing other structures for carrying out the same purposes. It should also be realized by those skilled in the art that such equivalent constructions do not depart from the spirit and scope of the appended claims. The novel features, both as to organization and method of operation, together with further objects and advantages will be better understood from the following description when considered in connection with the accompanying figures. It is to be expressly understood, however, that each of the figures is provided for the purpose of illustration and description only and is not intended as a definition of the limits of the appended claims.

BRIEF DESCRIPTION OF THE DRAWINGS

FIGS. 10 and 11 respectively depict a percutaneous lead and a paddle lead with field effect electrodes according to some representative embodiments.

FIG. 12 depicts an electrode encircled by a field effect electrode according to one representative embodiment.

DETAILED DESCRIPTION

A number of publications have reported theoretical results of the application of electrical stimulation to neural tissue within the spinal cord based upon computer modeling.

For example, the article "Transverse tripolar spinal cord stimulation: Theoretical performance of a dual channel system," by J. J. Struijk and J. Holsheimer, Journal Medical and Biological Engineering and Computing, Vol. 34, No. 4, pp. 273-279, (July 1996) describes a volume conductor model of the spinal cord and related structures. The three dimension model described in this paper was based upon MRI scans of the human spine at different vertebrae levels. From the MRI scans, different tissue types were identified and different conductivities were assigned to various finite spatial divisions within the three dimensional model. After defining potential differences applied or currents flowing between various electrodes of a stimulation lead, a three dimensional potential field was calculated using numerical methods. Additionally, models of neural tissue were utilized to determine the effect of the potential field on selected nerves within the spinal cord. By utilizing these models and numerical methods, predictions were made regarding which fibers would be stimulated in response to electrical pulses of various amplitudes using a number of different electrode combinations.

Figure 1:
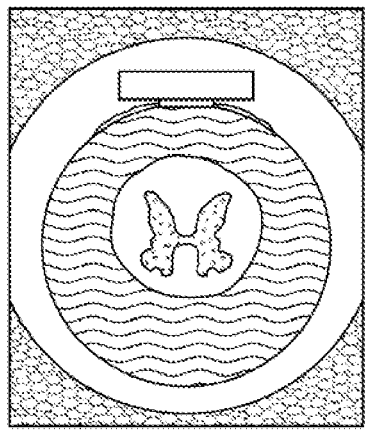
FIG. 1 depicts a model of a low thoracic level within the spinal cord using for simulation modeling of neurostimulation systems.

FIG. 1 depicts model 100 of a low thoracic level within the spinal cord. As seen in model 100, the neural tissue is defined within the interior and includes gray and white matter. The dorsal columns of white matter represent the neural tissue to be stimulated by SCS. An electrical contact of electrode is shown against the dura. The electrical contact is supported by a substrate of insulation. Cerebrospinal fluid surrounds the neural tissue within the dura. The cerebrospinal fluid possesses high conductivity relative to the white matter of the dorsal columns.

Figure 2:
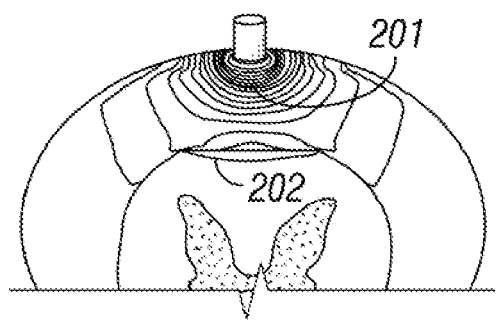
FIGS. 2 and 3 depict results from simulation modeling of the application of a stimulation pulse to the model shown in FIG. 1.
Figure 3:
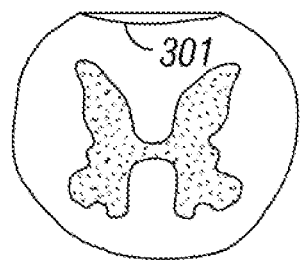

FIG. 2 depicts iso-current density lines generated in response to a stimulation pulses using computer model 100. As seen in FIG. 2, the current density is greatest in region 201. Only a relatively small relative amount of current is present in region 202 corresponding to the white matter of the dorsal columns. FIG. 3 depicts the predicted recruitment of neural tissue in response to the stimulation pulse used to generate the iso-current graph of FIG. 2. Contour 301 represents the depth of neural tissue where action potentials occur. As seen in FIG. 3, only neural tissue on the immediate surface of the dorsal columns is stimulated.

Based upon such theoretical studies, traditional spinal cord stimulation (SCS) techniques are believed to only deliver about 5-10% of the current supplied by the pulse generator to the neural tissue to be stimulated. Specifically, the majority of the current is believed to flow within the relatively high conductivity cerebrospinal fluid. Accordingly, there is a large loss of energy because the majority of the current cannot reach the desired neural tissue. Additionally, the electrode surface areas are required to be of undue size to safely conduct the high currents necessary to achieve the desired current density in the white matter of the dorsal columns.

"Tripolar" stimulation techniques have been proposed to achieve improved stimulation results. Tripolar stimulation techniques involve placing anodes on either side of a central cathode to limit the field distribution generated by the cathode. Tripolar stimulation techniques have been asserted to allow deeper recruitment of white matter within the spinal cord. Also, tripolar stimulation techniques have been asserted to allow discrimination between stimulation of the dorsal column and dorsal root fibers. However, it has been reported that tripolar stimulation techniques impose relatively high current drain as compared to conventional stimulation techniques. Specifically, it is estimated that approximately 10% of the current flows within the spinal cord for conventional monopolar and bipolar techniques while only approximately 5% of the current flows within the spinal cord for transverse tripolar techniques.

Some representative embodiments are directed to a stimulation lead that includes one or several field-effect electrodes. As used herein, a field-effect electrode is an electrode that is adapted to effect the electric field within the proximity of the electrode substantially without allowing current to flow through the field-effect electrode. By using such a field-effect electrode, some representative embodiments permit stimulation techniques that permit greater current to reach the neural tissue of the patient. Specifically, the field-effect electrode is used to exert force on charge carriers, such as electrons or ions, without contributing to or removing current from the stimulation current. By exerting force on the charge carriers, a greater amount of charge carriers can be "steered" into the neural tissue of the spinal cord. By causing a greater amount of current to reach the neural tissue of the patient, stimulation systems require less power to achieve similar therapeutic results. Accordingly, stimulation systems employing field-effect electrodes may possess smaller batteries and, hence, can possess a relatively smaller device profile which is desirable in implantable medical devices. Moreover, stimulation systems employing field-effect electrodes may be operated for longer periods of time without requiring recharging operations and/or replacing the system battery.

Figure 4:
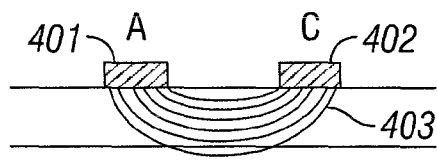
FIG. 4 depicts a conventional arrangement of an anode, a cathode, and current flow therebetween.
Figure 5:
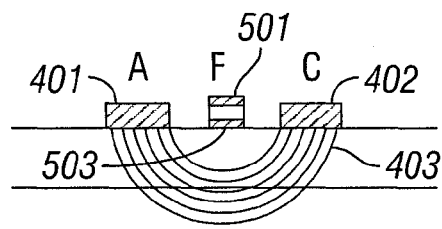
FIG. 5 an anode, cathode, a field effect electrode, and current flowing between the anode and cathode as affected by the field effect electrode according to one representative embodiment.

To illustrate the steering-capability of some representative embodiments, reference is made to FIGS. 4-7. FIG. 4 depicts a conventional arrangement of an electrode 401 (functioning as an anode) and electrode 402 (functioning as a cathode). As seen in FIG. 4, when a pulse is applied to current flows from anode 401 to cathode 402 (conceptually depicted by lines 403). The majority of the current flows within the cerebrospinal fluid. FIG. 5 depicts a similar arrangement of anode 401 and cathode 402. However, in FIG. 5, field effect electrode 501 is disposed between anode 401 and cathode 402. In FIG. 5, field effect electrode 501 is biased (e.g., by being coupled to an appropriate source) and applies an electric field. However, current does not flow to or from field effect electrode 501. For example, a thin insulative layer could be applied over a metal contact of field effect electrode 501 to prevent the current flow. The electrical field applied by field effect electrode 501 is believed to prevent substantial flow of electrons or negatively charged ions from flowing within region 503 proximate to field effect electrode 501. Accordingly, less electrons and negatively charged ions flow within the cerebrospinal fluid and more electrons and negatively charged ions are believed to be "pushed" deeper within the spinal cord tissue.

Figure 7:
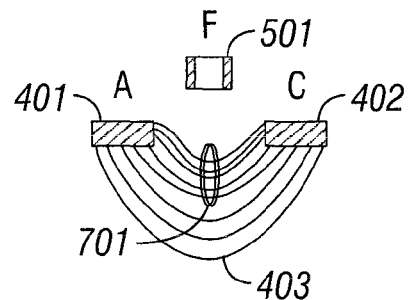
FIG. 7 depicts current flow when the field effect electrode is offset relative to the anode and cathode according to another representative embodiment.
Figure 6:
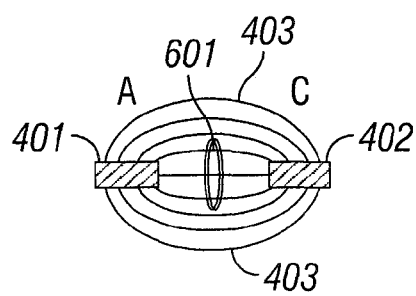
FIG. 6 depicts a "top view" of current flow for the electrode arrangement shown in FIG. 5.

FIGS. 6 and 7 depict the expected potential of field effect electrodes to steer current in a lateral or longitudinal direction relative to the spinal cord. In FIG. 6, a "top view" of anode 401 and cathode 402 is shown. Lines 403 represent current flow between anode 401 and cathode 402. Region 601 represents a locus of stimulation of the spinal cord between anode 401 and cathode 402. The locus of stimulation is the region of neural tissue that experiences action potentials in response to the stimulation pulse associated with the current.

FIG. 7 depicts a similar arrangement of anode 401 and cathode 402. In FIG. 7, field effect electrode 501 is offset relative to anode 401 and cathode 402. Field effect electrode 501 functions in the same manner as previously discussed. However, due to the relative positioning of field effect electrode 501 to anode 401 and cathode 402, the current flow is also steered longitudinally relative to field effect electrode 501. Accordingly, locus 701 of stimulation is shifted relative to anode 41 and cathode 402.

It shall be appreciated that the degree of steering generated by field effect electrode 501 is dependent upon the strength of the electrical field caused by field effect electrode 501. Accordingly, if a greater amount of steering is desired, a greater bias can be applied to field effect electrode 501. Conversely, if a smaller amount of steering is desired, a lesser bias can be applied.

Figure 8:
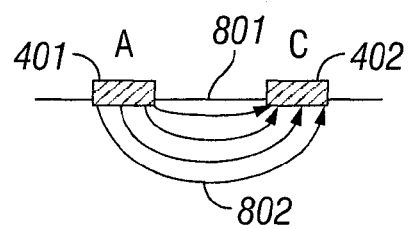
FIG. 8 depicts typical current density between an anode and a cathode.

The use of field effect electrodes 501 is useful to control other characteristics of current flow according to some representative embodiments. Referring now to FIG. 8, conventional anode 401 and cathode 402 arrangements cause a greater amount of current 801 to flow between the adjacent edges of the anode 401 and cathode 402 as opposed to the current flow 802 between the exterior edges.

Figure 9:
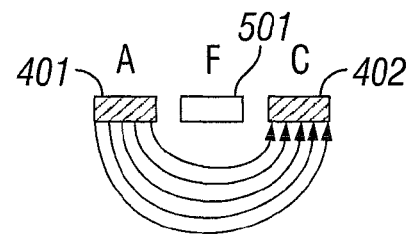
FIG. 9 depicts current density between an anode and a cathode with a field effect electrode disposed between the anode and cathode according to one representative embodiment.

In such cases, a greater current density is present at the edges of the anodes 401 and cathode 402. In operation of a stimulation system, the current density on an electrode must be kept within acceptable limits to prevent damage to the electrode and to prevent tissue trauma. As shown in FIG. 9, the current flow is more perpendicular to the electrode surfaces thereby reducing the "edge-effects" experienced by conventional stimulation techniques. Accordingly, because the current density is more uniform over the electrode surfaces, a greater amount of current can be applied without exceeding current density limits at the edges of anode 401 and cathode 402.

Stimulation leads comprising one or more field effect electrodes are preferably fabricated by (i) first using any conventional known lead fabrication technique or any later developed fabrication technique to create a lead with conventional electrodes and, then, (ii) adapting one or more of the conventional electrodes to function as field effect electrodes. In representative embodiments, conventional electrodes are adapted to function as field effect electrodes by applying a thin dielectric coating to the electrodes to prevent current flow from those electrodes.

FIG. 10 depicts percutaneous lead 1000 according to one representative embodiment. Lead 1000 comprises lead body 1006 of a suitable insulative material. Wire conductors (not shown) are preferably encapsulated or embedded within lead body 1006. Any suitable process for fabricating lead body 1006 may be utilized. For example, the fabrication process may comprise (i) extrusion of insulative material, (ii) followed by wrapping of insulative coated conductive wires, (iii) extrusion of additional insulative material, and (iii) application of heat and pressure to fuse the various insulative material(s) using shrink wrap material. Such fabrication processes are discussed in greater detail in U.S. patent application Ser. No. 10/630,233, filed Jul. 29, 2003, entitled "System and Method for providing a dual wrap lead body with inner and outer extrusion," which is incorporated herein by reference.

Lead 1000 comprises distal end 1001 and proximal end 1002. Distal end 1001 is the end of lead 1000 that is adapted for positioning proximate to neural tissue of the patient. Proximal end 1002 is the end that is adapted for electrical coupling to a pulse generator or an "extension" electrical connector.

Conventional electrodes 1003 and field effect electrodes 1004 are disposed on the distal end 1001 of lead 1000. Each pair of conventional electrodes 1003 is separated by a respective field effect electrode 1004 in the specific embodiment of FIG. 10. Other patterns of electrodes 1003 relative to field effect electrodes 1004 could be employed for other embodiments. As shown in FIG. 10, the width of field effect electrodes 1004 is smaller than the width of electrodes 1003. Specifically, the surface area of field effect electrodes 1004 can be smaller, because substantially no current flows to or from these electrodes 1004 and, hence, current density limitations are not an issue for these electrodes 1004. Any suitable surface area could be employed as suitable for a given lead design.

Each electrode 1003 is preferably electrically coupled to a corresponding terminal 1005 through one of the wire conductors within lead body 1006. Field effect electrodes 1004 can be electrically coupled to a common terminal 1005 through a wire conductor according to one representative embodiment. Alternatively, each field effect electrode 1004 could be electrically coupled to its own distinct terminal 1005 through a respective wire conductor according to another representative embodiment.

Conventional electrodes 1003, field effect electrodes 1004, and terminals 1005 can be fabricated on lead body 1006 utilizing any suitable known technique. For example, electrode and terminal spacers of insulative material can be employed to separate adjacent electrodes and terminals, overmolding applied, and centerless grinding applied to achieve an iso-diameteric lead profile as disclosed in U.S. Pat. No. 6,216,045, which is incorporated herein by reference. A dielectric coating is applied for field effect electrodes 1004 after their fabrication of the metal ring portion to prevent current flow to and from these electrodes 1004.

Laminotomy leads may also employ field effect electrodes 1004 according to some representative embodiments. FIG. 11 depicts example laminotomy lead 1100 according to one representative embodiment. Laminotomy lead 1100 comprises paddle structure 1110 adapted for implantation within a patient proximate to neural tissue to be stimulated. Paddle structure 1110 is preferably fabricated using a biostable, biocompatible insulative material. A nylon mesh, a fiberglass substrate, or the like (not shown) can be internalized within the paddle structure 1110 to increase its overall rigidity and/or to cause paddle structure 1110 to assume a prescribed cross-sectional form.

Electrodes 1101 and field effect electrodes 1102 are fabricated on a surface of paddle structure 1110. Electrodes 1101 and field effect electrodes are electrically coupled to terminals 1005 using wire conductors (not shown) within lead body 1006. In FIG. 11, the field effect electrodes are shown using a darkened interior surface, because only a subset of electrodes 1101 and field effect electrodes 1102 are annotated with reference numerals for the sake of clarity. Field effect electrodes 1102 are fabricated in much the same manner as electrodes 1101 with the exception of the dielectric coating applied to field effect electrodes 1102. As shown in FIG. 10, each adjacent pair of electrodes 1101 is separated by a respective field effect electrode 1102. In an alternative embodiment, field effect electrodes 1102 could take the form of an electrode that encircles a conventional electrode (see FIG. 12) in a manner similar to the design shown in U.S. Pat. No. 6,754, 539, which is incorporated herein by reference.

Figure 14:
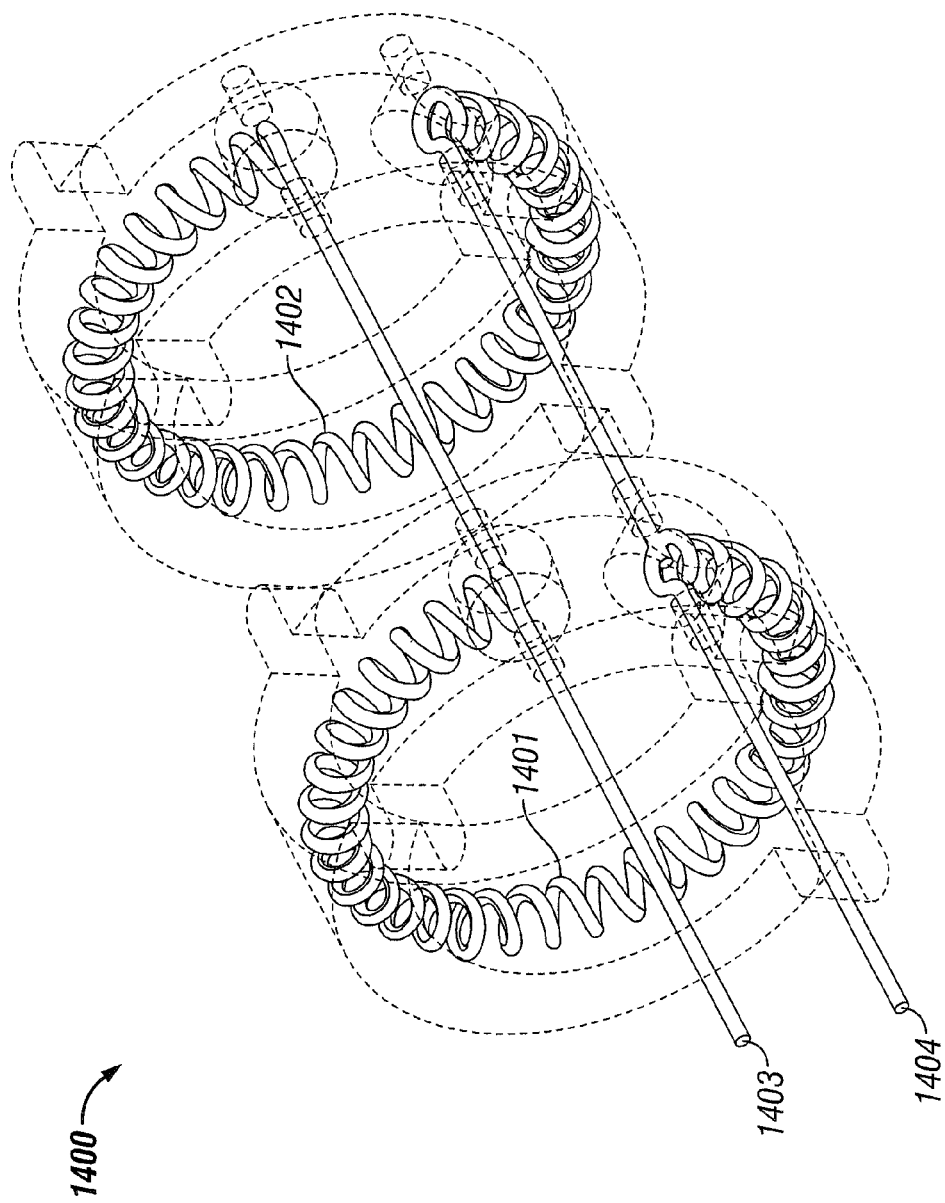
FIG. 14 depicts an assembly for generating a magnetic field that may be disposed about a lead body of a stimulation lead according to one representative embodiment.

In an alternative embodiment, in lieu of or in addition to field effect electrodes, one or more inductive coils may be employed on paddle structure 1110 for use in applying a force to charge carriers to shape the field resulting from applied stimulation pulses. In another alternative embodiment, a percutaneous lead could employ one or more inductive coils. FIG. 14 depicts assembly 1400 that may be disposed about a lead body of a stimulation lead according to one representative embodiment. Assembly comprises coils 1401 and 1402 embedded within insulative material. Coils 1401 and 1402 are electrically coupled to conductive extensions 1403 and 1404. Assembly 1400 may be placed over a lead body of a stimulation lead such that coils 1401 and 1402 are disposed adjacent to an electrode. Conductive extensions 1403 and 1404 can be electrically coupled to selected internal wire conductors of the lead body. Although inductors are used in a stimulation lead to generate a magnetic field for this described embodiment, one or more permanent magnets could be substituted according to other embodiments.

Although only two columns of electrodes 1101 are shown in FIG. 10, any suitable number of columns can be employed. In fact, because additional current reaches the neural tissue according to some representative embodiments, the surface area of electrodes 1101 can be reduced relative to conventional electrodes. Accordingly, the reduced surface area permits additional columns of electrodes 1101 to be more readily fabricated on a paddle structure adapted for insertion within the epidural space. The additional number of columns of electrodes permits greater resolution in the recruitment of specific dorsal column fibers within the spinal cord. The greater degree of specificity in recruitment of such dorsal column fibers enables electrical stimulation therapy to be accurately tailored to the specific condition and/or physiology of a given patient.

Figure 13:
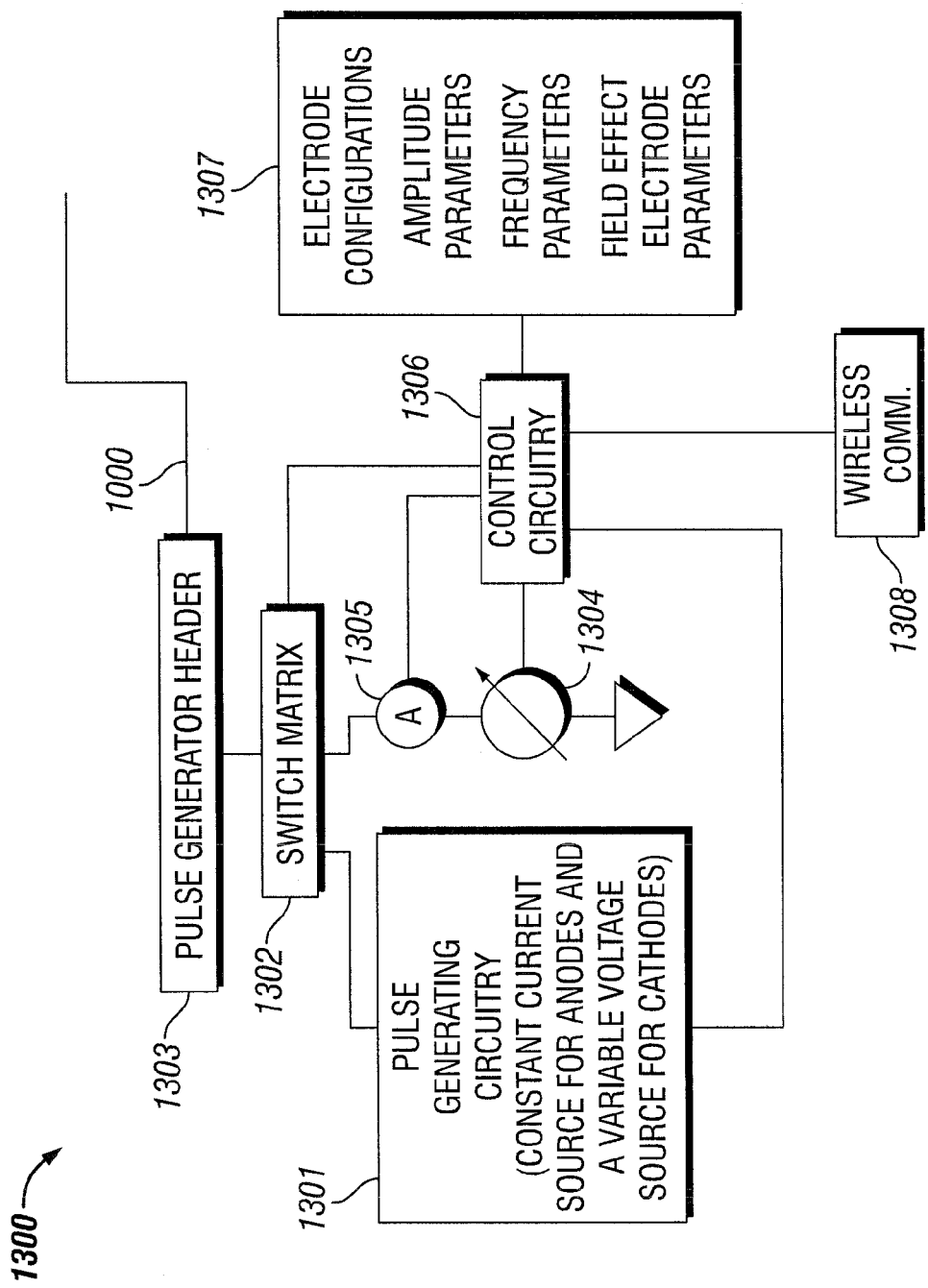
FIG. 13 depicts a stimulation system including a pulse generator adapted to control one or more field effect electrodes according to one representative embodiment.

FIG. 13 depicts a block diagram of circuitry for pulse generator 1300 that is adapted to apply electrical fields within a patient using field effect electrodes while applying pulse(s) to tissue of the patient according to one representative embodiment.

Pulse generator 1300 comprises pulse generator header 1303 for coupling to one or more stimulation leads (or lead "extensions"), percutaneous stimulation lead 1000 as an example. The term "header" is used in the art, because the header is usually disposed on an upper surface of the metallic housing (although the header can be disposed anywhere on the device as long as it is reasonably accessible). The header typically comprises a plurality of connector structures for electrically connecting to the terminals of a stimulation lead. The connector structures are contained within a suitable housing of epoxy and/or various polymers. The connector structures are electrically connected to feedthrough wires to switch matrix 1302. Switch matrix 1302 controllable switches the outputs from pulse generating circuitry 1301 and variable voltage source 1304 to the respective feedthrough wires (not shown) connecting to pulse generator header 1303.

Any suitable pulse generating design may be employed according to some embodiments. Multiple voltage or current sources could be employed. In the embodiment shown in FIG. 13, pulse generating circuitry 1301 comprises a constant current source for anodes and a variable voltage source for cathodes. Example circuitry that could be employed in pulse generating circuitry 1301 is described in U.S. Patent Publication No. 20060170486 entitled "PULSE GENERATOR HAVING AN EFFICIENT FRACTIONAL VOLTAGE CONVERTER AND METHOD OF USE," which is incorporated herein by reference.

In a preferred embodiment, control circuitry 1306 couples variable voltage source 1304 to one or more field effect electrodes while one or more electrical pulses are being delivered to tissue of the patient. Control circuitry 1306 may comprise a microprocessor and suitable software. Also, control circuitry 1306 may comprise multiple circuits distributed within pulse generator 1300. Alternatively, control circuitry 1306 may be integrated within an application specific integrated circuit.

In operation, control circuitry 1306 preferably accesses stimulation parameters stored in memory 1307. The stimulation parameters may include one or more electrode configuration parameters, amplitude parameters, frequency parameters, field effect electrode parameters, etc. The stimulation parameters may be encoded in terms of "stim sets" and/or "stimulation programs" which are known in the art. Control circuitry 1306 controls the amplitude of pulses applied by pulse generating circuitry 1301 in response to the parameters. Likewise, control circuitry 1306 controls switch matrix in response to the parameters. In regard to controlling field effect electrodes, control circuitry 1306 sets the voltage of variable voltage source 1304 in response to one or more parameters. Additionally, control circuitry 1306 controls switch matrix 1302 to electrically couple variable voltage source 1304 to one or more appropriate field effect electrodes at the appropriate time. In another embodiment, a fixed voltage source could be alternatively or additionally employed to bias one or more field effect electrodes. The fixed voltage source could be implemented in dedicated circuitry within the pulse generator. Alternatively, the fixed voltage source may utilize a potential that is used for multiple functions within the pulse generator. Although a constant voltage is contemplated for application to a field effect electrode in conjunction with the application of a stimulation pulse on other electrodes, other waveforms could be applied to the field effect electrode. A pulse waveform, sawtooth waveform, a sinsusoidal-like waveform, and/or the like could be applied for field effect electrodes as examples.

Control circuitry 1306 preferably controls the application of a steering voltage to field effect electrodes using current meter 1305. Specifically, when control circuitry 1306 connects variable voltage source 1304 to one or more field effect electrodes, control circuitry 1306 monitors any current flowing between voltage source 1304 and the field effect electrodes. Specifically, if the dielectric material associated with one or more field effect electrodes is compromised or damaged thereby allowing current to flow to the patient through the field effect electrodes, control circuitry 1306 can detect the compromise by detecting current flow from voltage source 1304. To protect the patient from pain and/or injury, control circuitry 1306 preferably sets a high impedance state (e.g., opens one or more switches in switch matrix 1302) between voltage source 1304 and the one or more field effect electrodes. Additionally, control circuitry 1306 preferably communicates that one or more field effect electrodes are not functioning properly to an external patient or clinician programmer device (not shown) using wireless communication circuitry 1308

Figure 15A:
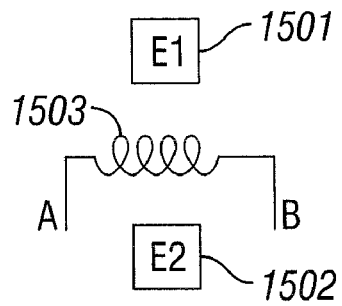
FIGS. 15A-15C depict electrodes, an inductive coil, and a generator adapted for steering of current utilizing a magnetic field according to one alternative embodiment.
Figure 15B:
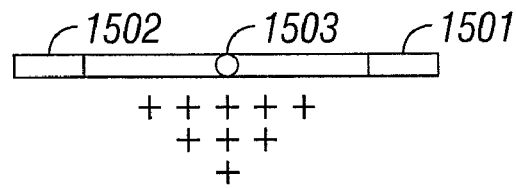
Figure 15C:
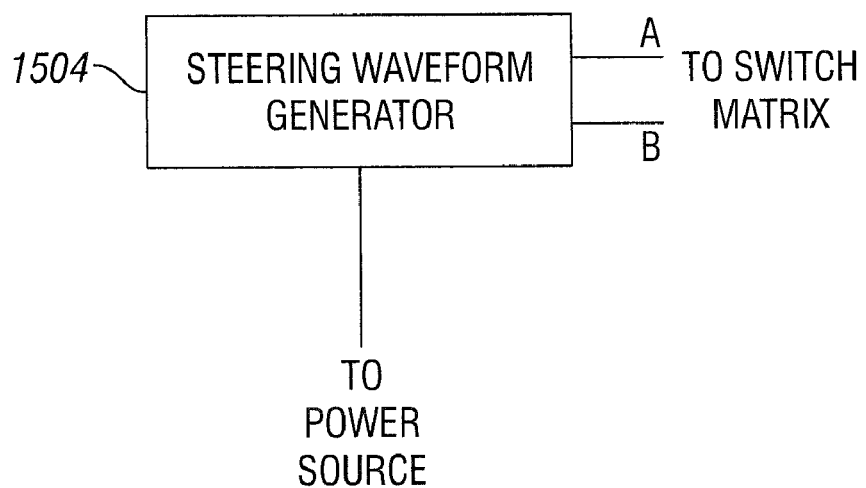

FIGS. 15A-15C depict electrodes 1501, 1502, inductive coil 1503, and generator 1504 adapted for steering of current utilizing a magnetic field according to one alternative embodiment. In FIG. 15A, a top view of electrodes 1501 and 1502 disposed about inductive coil 1503 is shown. FIG. 15B shows a side view of electrodes 1501, 1502 and coil 1503. In FIG. 15B, the magnetic field created by coil 1503 is generally oriented into the page. FIG. 15C depicts steering waveform generator 1504. Generator 1504 is preferably adapted to generate high frequency pulses of current to drive inductor 1503. Generator 1504 is preferably disposed within an IPG for connection to a switch matrix of the IPG to deliver the current to inductor 1503 to generate a magnetic field.

The generated magnetic field is somewhat localized due to the strength of the field. Electrons within the localized magnetic field tend to flow along an extended path due to the magnetic field. Specifically, electrons experience force caused by the electric field due to the potentials present on electrodes 1501 and 1502 during a stimulation pulse. Also, (as defined in the Lorentz force equation), the electrons experience a force from the magnetic field that is related to the instantaneous velocity of the electrodes and the magnetic field. The combination of forces cause the electrodes to flow along a somewhat cycloid trajectory. It is believed that the cycloid trajectory causes the electrons to experience greater impedance within the magnetic field due to the longer path of electron flow between electrodes 1501 and 1502. Thereby, the greater impedance within the localized magnetic field is believed to cause relatively greater electron flow outside of the localized magnetic field.

Although certain embodiments have been described in terms of spinal cord stimulation (SCS), other representative embodiments may employ field-effect electrodes or magnetic elements to steer current to stimulate other tissue within the body. For example, some representative embodiments may be employed to steer current to stimulate neural tissue in a deep brain location, cortical neural tissue, peripheral nerve tissue, etc.

Although certain representative embodiments and advantages have been described in detail, it should be understood that various changes, substitutions and alterations can be made herein without departing from the spirit and scope of the appended claims. Moreover, the scope of the present application is not intended to be limited to the particular embodiments of the process, machine, manufacture, composition of matter, means, methods and steps described in the specification. As one of ordinary skill in the art will readily appreciate when reading the present application, other processes, machines, manufacture, compositions of matter, means, methods, or steps, presently existing or later to be developed that perform substantially the same function or achieve substantially the same result as the described embodiments may be utilized. Accordingly, the appended claims are intended to include within their scope such processes, machines, manufacture, compositions of matter, means, methods, or steps.

The invention claimed is:

1. A method of electrically stimulating neural tissue of a patient, comprising:
   generating, by an implantable pulse generator, one or more electrical pulses;
   applying the one or more electrical pulses to neural tissue of a patient using one or more electrodes of one or more stimulation leads;
   concurrently with the generating, providing a voltage waveform or signal by the implantable pulse generator; and
   concurrently with the applying, electrically coupling one or more field effect electrodes of the one or more stimulation leads to the voltage waveform or signal to generate a localized electric field within tissue proximate to the one or more electrodes used to apply the one or more electrical pulses to steer the one or more electrical pulses deeper into patient tissue, wherein the one or more field effect electrodes are adapted to prevent conduction of current through the one or more field effect electrodes.

2. The method of claim 1 further comprising:
   operating circuitry for measuring current within the implantable pulse generator to detect current flow through the one or more field effect electrodes.

3. The method of claim 2 further comprising:
   disconnecting the one or more field effect electrodes from the bias in response to a signal from the circuitry for measuring.

\* \* \* \* \*